(12) United States Patent
Rafter et al.

(10) Patent No.: US 6,436,045 B1
(45) Date of Patent: Aug. 20, 2002

(54) USER CONTROLLED DESTRUCTIVE WAVEFORM ROUTINE FOR ULTRASOUND SYSTEMS

(75) Inventors: Patrick G Rafter, Windham, NH (US); George A Brock-Fisher; Mckee D Poland, both of Andover, MA (US)

(73) Assignee: Koninklijke Phillips Electronics N.V., Eindhoven (NL)

( * ) Notice: Subject to any disclaimer, the term of this patent is extended or adjusted under 35 U.S.C. 154(b) by 0 days.

(21) Appl. No.: 09/559,446

(22) Filed: Apr. 27, 2000

(51) Int. Cl.[7] .............................................. A61B 8/00
(52) U.S. Cl. ...................................... 600/447; 600/459
(58) Field of Search ................................ 600/437, 443, 600/447, 458, 459

(56) References Cited

U.S. PATENT DOCUMENTS

| | | | | |
|---|---|---|---|---|
| 5,694,937 A | | 12/1997 | Kamiyama | 128/661 |
| 5,735,281 A | | 4/1998 | Rafter et al. | 128/662 |
| 5,944,666 A | * | 8/1999 | Hossack et al. | 600/458 |
| 5,957,845 A | * | 9/1999 | Holley et al. | 600/440 |
| 6,149,597 A | * | 11/2000 | Kamiyama | 600/458 |
| 6,196,973 B1 | * | 3/2001 | Lazenby et al. | 600/458 |
| 6,210,333 B1 | * | 4/2001 | Gardner et al. | 600/450 |
| 6,210,335 B1 | * | 4/2001 | Miller | 600/454 |
| 6,217,516 B1 | * | 4/2001 | Poland et al. | 600/437 |
| 6,238,341 B1 | * | 5/2001 | Mullen | 600/437 XL |

FOREIGN PATENT DOCUMENTS

WO    WO98/47533    10/1998

* cited by examiner

*Primary Examiner*—Francis J. Jaworski

(57) ABSTRACT

An ultrasound system with a transducer that transmits ultrasound signals based on a plurality of parameters in response to a control device that, upon activation in a first imaging mode, adjusts at least one of the parameters to cause the transducer to output a modified waveform based on the first imaging mode, for example, to output a signal adapted to disrupt contrast agent while in a lower power imaging mode or to output a signal adapted for continuous low power viewing when in a triggered mode. Subsequently, the control device readjusts the parameters so as to cause the transducer to output a waveform adapted to the first imaging mode.

20 Claims, 7 Drawing Sheets

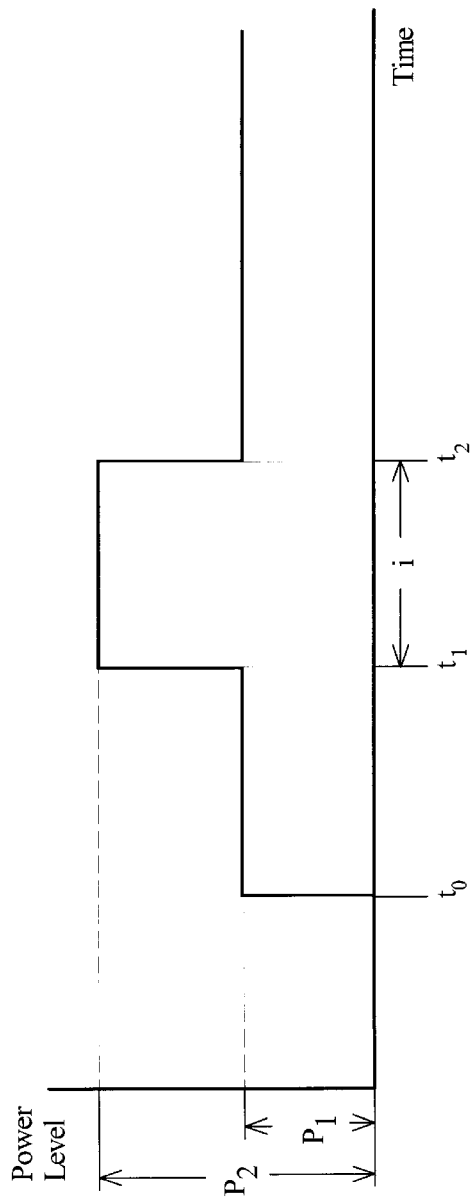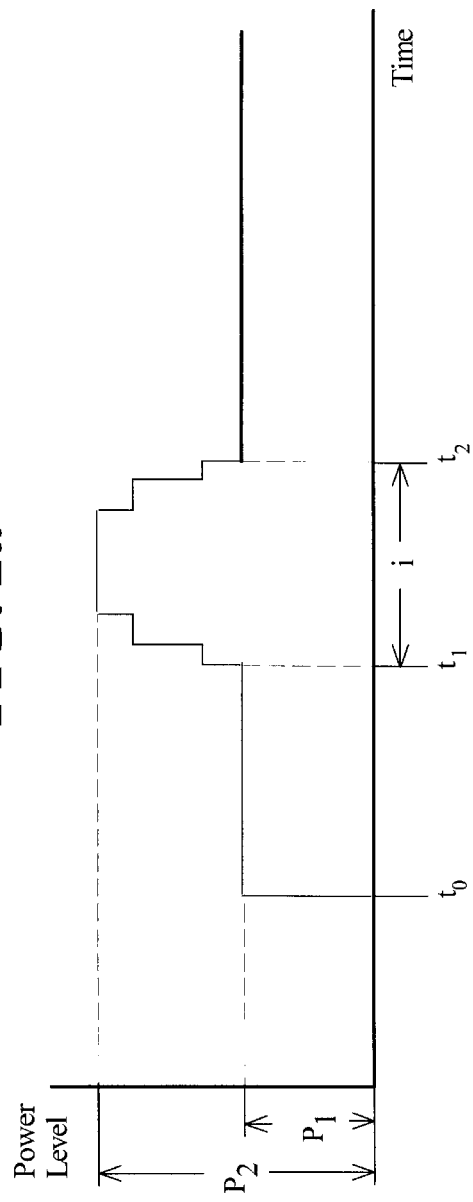

USER CONTROLLED DESTRUCTIVE WAVEFORM ROUTINE FOR ULTRASOUND SYSTEMS

BACKGROUND OF THE INVENTION

The present invention relates to method and apparatus which, under user control, modify an ultrasound system's output waveform to efficiently disrupt contrast agent and subsequently returns the waveform to a predefined format.

Current ultrasonic imaging systems make use of contrast agents in circulation to enhance ultrasound returns. Contrast agents are substances which strongly interact with ultrasound waves and return echoes which may be clearly distinguished from those returned by blood and tissue. The most popular contrast agents are microbubbles which, using known algorithms, provide a readily detectable nonlinear behavior in certain acoustic fields. Microbubbles are especially useful for imaging the body's vascular system by injection into veins and arteries, from which they are subsequently filtered by the lungs, kidneys and liver. Microbubbles generally comprise coated gas bubbles. The coating shells serve to protect the gas from diffusion into the blood stream, making the microbubbles stable in the body for a significant period of time.

The shells of the microbubbles can be caused to rupture, thereby producing an easily distinguishable echo, by appropriately adjusting the output waveform of an ultrasonic transducer. Known ultrasound systems and methods only change one parameter, power, in the output waveform to rupture microbubbles. The present inventors have recognized that a variety of parameters can be adjusted to optimize the rupturing of microbubbles. In any event, for purposes of the present invention, the most significant feature of contrast agents is that not only do they produce an easily detectable echo when isonified with low MI ultrasound, but they also produce an easily distinguishable echo when they are burst with high MI ultrasound. This behavior makes contrast agents equally useful in two popular imaging modes: low power imaging and triggered imaging.

Low power imaging modes use a low MI signal to simply watch contrast agent travel with the blood flow in a region of interest (ROI). In situations of rapid replenishment, such as when imaging a heart chamber, an acoustic power level of around 0.5 MI, is used to reduce the destruction of the contrast agent to a point where circulatory replenishment is sufficient to keep the cavity well opacified. In situations where the circulatory replenishment is much slower, such as in myocardial tissues, the power level must be reduced even further, so as to keep a sufficient number of non-disrupted bubbles in view.

The low power imaging mode becomes even more valuable when all of the contrast agents within the ROI are ruptured (or "disrupted"), as with a high MI ultrasound pulse, and the sonographer can watch the re-introduction of contrast agent into the ROI. This allows an analysis of the rate of blood flow and, more particularly, perfusion. However, it is difficult for a sonographer to quickly and accurately set parameters in the ultrasound system to produce a waveform that bursts the contrast agent and then reset the affected parameters back to the values required by the low power imaging mode. Sonographers typically push slide controls affecting the power output of the transducer to a maximum level and then pull them back into position. Not only is this an inexact procedure, but only adjusts the power of the ultrasound signal, which results in an inefficient use of acoustic power.

The triggered imaging mode generates high MI pulses at a timing dictated by a physiological signal, such as an ECG signal. The resulting image clearly shows the bursting of the contrast agent. While this is useful in and of itself, it becomes more useful when a series of images are produced at different timing. For example, producing one image at a first heart beat, skipping the next heat beat and producing a second image, skipping two heartbeats and producing a third image, skipping three heartbeats and producing a fourth image, etc . . . Such a series of images can be analyzed to plot a rate of blood flow and, more particularly, perfusion.

The triggered imaging mode requires a high degree of competence on the part of the sonographer. In between triggered frames, the image is frozen to the last frame. Thus, the sonographer must wait an increasing amount of time between images to re-establish visual confirmation of the imaging plane. Even with real time visual feedback (as in the low power imaging mode), it takes a great deal of patience and practice to hand hold the transducer against a patient without disrupting the imaging plane. Without visual feedback (as in the triggered mode), it is extremely difficult to control the transducer so that the imaging plane is not disrupted. Many times the sonographer tries to exit the triggered mode and use the low power mode to re-establish real time visual contact, adjust the imaging plane and then re-enter the triggered mode to complete the image series. This activity requires the sonographer to change a variety of settings using a plurality of controls, such as the transmit power, gain, focus, mode, etc . . . This can be so time consuming that the sonographer is forced to give another injection of contrast agent to complete the procedure. More importantly, such readjustment can cause the series of images produce by the trigger mode to be flawed, thereby reducing the accuracy of the subsequent analysis.

Current medical ultrasonic imaging systems provide the sonographer with a control panel for adjusting the ultrasound transmission and reception. Various types of buttons and switches are used to set the imaging mode, parameters of the ultrasound signal, and display options. Such control panels typically provide analog style rotary or slide controls (the signals from such controls are typically digital) to adjust the parameters of the ultrasonic transmission. For example, controls to adjust the acoustic power (MI) of the ultrasound signal typically provide a 30 db range of control. Such analog style rotary and slide controls do not permit quick and accurate changes in acoustic power. Digital controls can be even more cumbersome to adjust quickly. Currently, adjusting parameters of the ultrasound signal alone, or in conjunction with a change of imaging mode, is a complicated, time-consuming operation.

The present inventors have recognized a need for an operator interface that provides automated procedures, activated by a sonographer, for adjusting parameters of the ultrasound signal.

SUMMARY OF THE INVENTION

A user interface for an ultrasound system that provides a user activated automated control for adjusting parameters of an ultrasound signal output from a transducer. The ultrasound system is provided with a transducer that transmits ultrasound signals at a plurality of acoustic power levels and in response to activation of a control device adjusts parameters of the ultrasound waveform to, for example, disrupt contrast agent or provide a low MI viewing mode, and after a predetermined time readjusts the output of the transducer to a predefined form. The control device is preferably a routine that may be activated by a sonographer with a simple button, such as a push button, toggle switch, soft button, voice activation, etc . . . The duration may be fixed or based on another control, such as a dial or slide, set by the operator. Likewise, the parameters of the waveform may be fixed or based on another control, such as a dial or slide, set by the operator. The predefined form to which the transducer returns after the predetermined time may be set to the form of the output at time of activation, a fixed form, or a form based on another control, such as a dial or slide, set by the operator.

BRIEF DESCRIPTION OF THE DRAWINGS

These and other objects and advantages of the invention will become apparent and more readily appreciated from the following description of the preferred embodiments, taken in conjunction with the accompanying drawings of which:

FIG. 2a is a signal chart showing the acoustic power during a low power imaging mode as controlled by the waveform control routine in accordance with the preferred embodiment of the present invention.

FIG. 2b is a signal chart showing the acoustic power during a low power imaging mode as controlled by the waveform control routine in accordance with another aspect of the preferred embodiment of the present invention.

DESCRIPTION OF THE PREFERRED EMBODIMENTS

Figure 1:
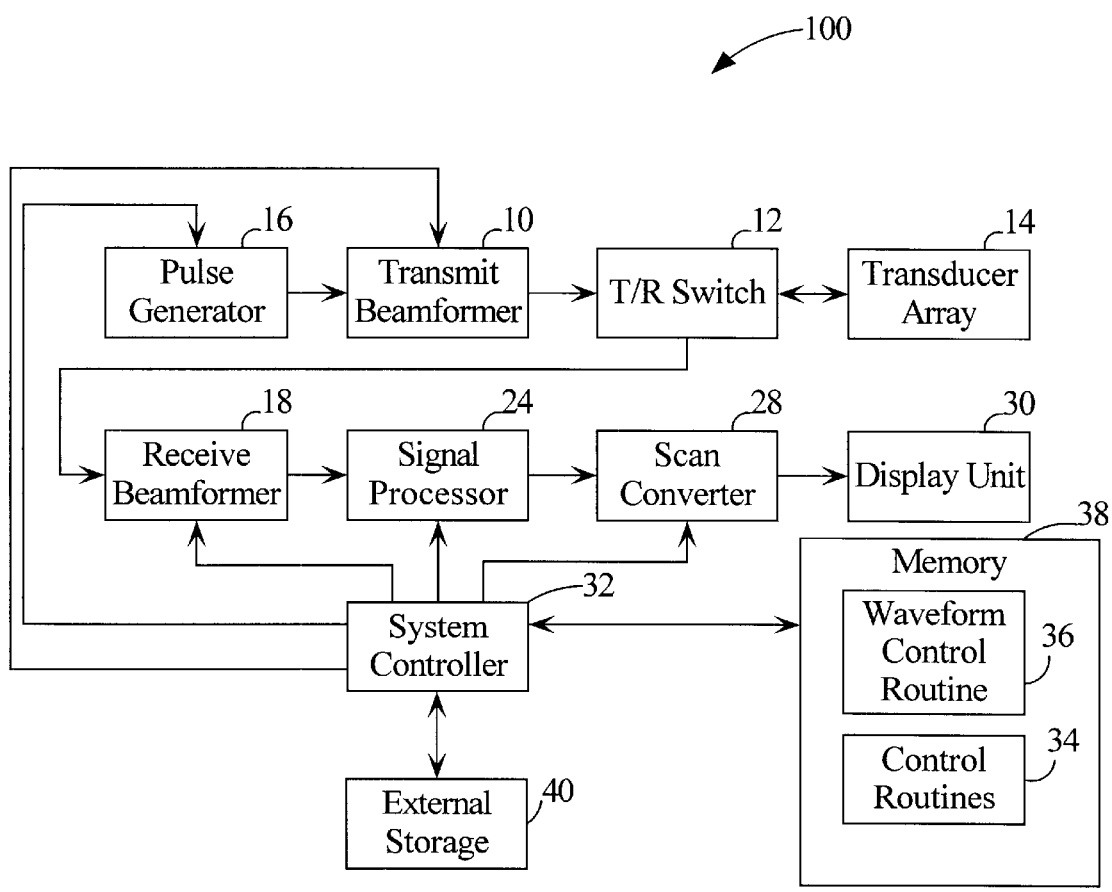
FIG. 1 is a simplified block diagram of an ultrasound imaging system in accordance with a preferred embodiment of the present invention.

Reference will now be made in detail to the present preferred embodiments of the present invention, examples of which are illustrated in the accompanying drawings, wherein like reference numerals refer to like elements throughout.

The invention is preferably embodied by an added user control to an ultrasound system, either as a soft key in a menu or as a hard key, such as a button or toggle switch. Activating this key causes an ultrasound waveform output by a transducer to be modified. If the ultrasound system is in the triggered mode, the waveform is modified to allow low power imaging (to provide a visual check of the imaging plane). If the ultrasound system is in the low power imaging mode, the waveform is modified for the disruption of contrast agent. A second activation of the key causes the system to reset, as rapidly as practical, to the original, user set waveform and/or mode. Alternatively, the reset can be automatic after a preset duration.

More generally, the present invention provides a user accessible waveform control routine for modifying a waveform of an ultrasound signal so as to, for example obtain a real-time view (which does not disrupt contrast agent) or efficiently disrupt contrast agent (to allow for subsequent real-time viewing of the reinsertion of contrast agent), maintaining the modified waveform for a set period of time, or for a set cycle, and then return the waveform to its pre-activation state. The waveform control routine can be activated in a variety of manners, for example buttons, real or soft, can be provided at a variety of location on ultrasound apparatus to trigger the waveform control routine and provide parameters for the execution of the waveform control routine. Further, other routines can be used to trigger the destructive waveform routine, such as a routine that triggers the destructive waveform in synchronization with an ECG signal.

The detailed description which follows is presented in terms of routines and symbolic representations of operations of data bits within a memory, associated processors, and possibly networks, and network devices. These descriptions and representations are the means used by those skilled in the art to effectively convey the substance of their work to others skilled in the art. A routine is here, and generally, conceived to be a self-consistent sequence of steps or actions leading to a desired result. Thus, the term "routine" is generally used to refer to a series of operations performed by a processor, be it a central processing unit of an ultrasound system, or a secondary processing unit of such an ultrasound system, and as such, encompasses such terms of art as "program," "objects," "functions," "subroutines," and "procedures."

In general, the sequences of steps in the routines require physical manipulation of physical quantities. Usually, though not necessarily, these quantities take the form of electrical or magnetic signals capable of being stored, transferred, combined, compared or otherwise manipulated. Those of ordinary skill in the art conveniently refer to these signals as "bits," "values," "elements," "symbols," "characters," "images," "terms," "numbers," or the like. It should be recognized that these and similar terms are to be associated with the appropriate physical quantities and are merely convenient labels applied to these quantities.

In the present case, the routines and operations are machine operations to be performed in conjunction with human operators. Useful machines for performing the operations of the present invention include the Agilent Technologies SONOS 5500 and other similar devices. In general, the present invention relates to method steps, software, and associated hardware including a computer readable medium, configured to store and/or process electrical or other physical signals to generate other desired physical signals.

The apparatus set forth in the present application is preferably specifically constructed for the required purpose, i.e., ultrasound imaging, but the methods recited herein may operate on a general purpose computer or other network device selectively activated or reconfigured by a routine stored in the computer and interface with the necessary ultrasound imaging equipment. The procedures presented herein are not inherently related to any particular ultrasonic system, computer or other apparatus. In particular, various machines may be used with routines in accordance with the teachings herein, or it may prove more convenient to construct more specialized apparatus to perform the required method steps. In certain circumstances, when it is desirable that a piece of hardware possess certain characteristics, these characteristics are described more fully in the following text. The required structures for a variety of these machines may appear in the description given below. Machines which may perform the functions of the present invention include those manufactured by such companies as AGILENT TECHNOLOGIES and ADVANCED TECHNOLOGY LABORATORIES, INC., as well as other manufacturers of ultrasound equipment.

With respect to the software described herein, those of ordinary skill in the art will recognize that there exists a variety of platforms and languages for creating software for performing the procedures outlined herein. Those of ordinary skill in the art also recognize that the choice of the exact platform and language is often dictated by the specifics of the actual system constructed, such that what may work for one type of system may not be efficient on another system.

FIG. 1 is a simplified block diagram of an ultrasound imaging system 100 in accordance with the preferred embodiment of the present invention. It will be appreciated by those of ordinary skill in the relevant arts that the ultrasound imaging system 100, as illustrated in FIG. 1, and the operation thereof as described hereinafter is intended to be generally representative such systems and that any particular system may differ significantly from that shown in FIG. 1, particularly in the details of construction and operation of such system. As such, the ultrasound imaging system 100 is to be regarded as illustrative and exemplary and not limiting as regards the invention described herein or the claims attached hereto.

A transmit beamformer 10 is coupled through a transmit/receive (T/R) switch 12 to a transducer array 14, which includes an array of transducer elements. The T/R switch 12 typically has one switch element for each transducer element. The transmit beamformer 10 receives transmit pulse sequences from a pulse generator 16. The transducer array 14, energized by the transmit beamformer, transmits ultrasound energy into a region of interest (ROI) in a patient's body and receives reflected ultrasound energy, or echoes, from various structures and organs within the patient's body. As is known in the art, by appropriately delaying the pulses applied to each transducer element by the transmit beamformer 10, a focused ultrasound beam is transmitted.

The transducer array 14 is coupled through the T/R switch 12 to a receive beamformer 18. Ultrasound energy from a given point within the patient's body is received by the transducer elements at different times. The transducer elements convert the received ultrasound energy to transducer signals which may be amplified, individually delayed and then summed by the receive beamformer 18 to provide a beamformer signal that represents the received ultrasound level along a desired receive line. The receive beamformer 18 may be a digital beamformer including an analog-to-digital converter for converting the transducer signals to digital values. As known in the art, the delays applied to the transducer signals may be varied during reception of ultrasound energy to effect dynamic focusing. The process is repeated for multiple scan lines to provide signals for generating an image of the region of interest in the patient's body. The receive beamformer 18 may, for example, be a digital beamformer of the type used in the AGILENT SONOS 5500 ultrasound system manufactured and sold by AGILENT TECHNOLOGIES.

The scan pattern may be a sector scan, wherein scan lines typically originate at the center of the transducer array 14 and are directed at different angles. Linear, curvilinear and other scan patterns may also be utilized. Furthermore, the scan pattern may be two-dimensional or three-dimensional. In an alternative system configuration, different transducer elements are used for transmitting and receiving. In that configuration, the T/R switch 12 is not required, and the transmit beamformer 10 and the receive beamformer 18 are connected directly to the respective transmit and receive transducer elements.

The beamformer signals are applied to a signal processor 24 which processes the beamformer signal for improved image quality. The receive beamformer 18 and the signal processor 24 constitute an ultrasound receiver. The output of the signal processor 24 is supplied to a scan converter 28 which converts sector scan or other scan pattern signals to conventional raster scan display signals. The output of the scan converter 28 is supplied to a display unit 30, which displays an image of the region of interest in the patient's body. In the case of a three-dimensional scan pattern, the scan converter 28 may be replaced by an image data buffer that stores the three-dimensional data set and a processor that converts the three-dimensional data set to a desired two-dimensional image.

A system controller 32 provides overall control of the system. The system controller 32 performs timing and control functions and typically includes a microprocessor operating under the control of control routines 34, including a waveform control routine 36, which are stored in a memory 38. As will be discussed in detail below, the waveform control routine 36 controls the functions of the pulse generator 16 to modify the output of the transducer array 14 to a form more conducive to non-destructive imaging (in the case of triggered mode scanning) or disrupting contrast agent (in the case of low powered imaging mode), and after a predetermined time returns the output of the transducer array 14 to a form suitable to the imaging mode being used. The system controller also utilizes a memory 38 to store intermediate values, including system variables describing the operation of the ultrasound imaging system 100. For example, the waveform control routine 36, when invoked, retrieves various parameters necessary for operation from the memory 38. External storage 40 may be utilized for more permanent and/or transportable storage of data. Examples of suitable external storage devices include a floppy disk drive, a CD-ROM drive, a videotape unit, etc . . .

The waveform control routine 36 may be configured to change a variety of parameters of the output waveform of the transducer array 14. The parameters that enable low power imaging are well known in the art. One aspect of the present invention presents a processor controlled waveform control routine that, when the ultrasound system is in a triggered mode, automatically modifies an output waveform to create a waveform suitable for viewing and subsequently returns the output to one suitable for triggered mode imaging. In conjunction therewith, during the low power viewing, the previous triggering sequence may be suspended.

In the case of low power mode imaging, wherein the periodic disruption of contrast agent is desirable, the present inventors have discovered that a variety of parameters contribute to the efficiency of disruption of contrast agent. Conventionally, only power has been adjusted when disrupting contrast agent. Perhaps this is because power is one of the easiest parameters to adjust on conventional ultrasound systems, the user simply rotates a dial, or moves one or more slide controls. This manual form of control presents two problems. First, it is imprecise, in that the user manually increases the power to full power and then returns the power to the previous level. If the sonographer is in a hurry, he or she may not even look at the position of the controls. The present invention presents a processor controlled waveform control routine that automatically modifies an output waveform to create a destructive waveform (for example by raising power) and returns to a waveform suitable for viewing. The present invention also provides alternatives to simply increasing power to disrupt contrast agent.

Basically, the present invention provides a control routine that, upon activation, modifies parameters of an output waveform. Then, upon reactivation (or at a predetermined time) either returns the parameters to their state prior to activation of the control routine or sets them to a predetermined state for subsequent imaging (based on the imaging mode of the ultrasound system at time of activation). The control parameters modified by the waveform control routine 36 may include parameters that control:

1) The envelope shape of the transmitted ultrasound signal pulse train. This refers to the format of the pulses on one line of output. Typically, the transmitted ultrasound signal pulse train is in the form of a Gaussian curve. However, the present inventors have determined that a rectangular shape is more efficient at disrupting contrast agent.

2) The frame rate of the image frames being acquired. The frame rate can be varied based upon an imaging mode, or simply to provide increased acoustic power.

3) The fundamental frequency of the transmitted ultrasound pulses. It has been found that certain types of contrast agent are more susceptible to destruction at certain frequencies. In the case of micro-bubbles, lower frequencies seem to cause more uniform destruction, with less attenuation, than higher frequencies. It appears that the lower the frequency the better the effect.

4) The duration of the transmitted ultrasound pulses. By adjusting the duration of each pulse, i.e., adjusting the number of transmit cycles, the amount of acoustic energy delivered per frame can be increased significantly. This allows for shortens the time required for the destruction routine.

5) The magnitude of the transmitted ultrasound pulses. In other words, increasing or decreasing the power or MI of the waveform. This is perhaps the most fundamental change that can be made to the waveform and may, in some circumstances, be the preferred modification.

6) The position of the transmit focus. Transmit focus can be controlled on a line by line or frame by frame basis. The focus of a transmit waveform is the subject of most of the acoustic energy output by the transducer array 14 and therefore forms a zone of destruction. By scanning or localizing the focus, disruption of contract agent can be more tightly controlled. For example, if the user has identified an ROI, the transmit focus can be scanned within the ROI to selectively destroy contrast agent therein. This has the benefit of reducing the acoustic energy received by the patient. It also has the benefit of reducing the time required for destruction, which reduces the load on the transducer array 14. Such scanning can be performed on a line by line basis, e.g., outputting one line a certain focus and then outputting another line (at the same location or another location) with a deeper focus.

7) The size of the transmit packet of ultrasound pulses. By increasing the number of pulses in a packet, the delivery of acoustical energy can be increased, thereby shortening the overall time required to disrupt contrast agent. Also, the packet sequence can be modified to produce packets which all exhibit high power. Generally, for low power imaging, pulses in a packet may be individually shaped to provide a gentle increase and decrease in power over the packet. Thus, when using the manual method of simply turning a dial or sliding a slider, the packet will still gradually increase and decrease over the packet sequence. As noted above this is not as effective as a rapid increase in power. To more effectively disrupt contrast agent, the pulses in a packet can be shaped to reach a full power level as quickly as possible.

8) The pulse repetition frequency of the transmitted ultrasound pulses. During imaging, the limiting factor in imaging frame rate is the time it takes a pulse to return. Ultrasound systems send out pulses at a frequency selected to allow for the reception of echos. When disrupting contrast agent, imaging is typically a secondary concern, if it is a concern at all. This allows the pulse repetition frequency to be increased, thereby delivering more ultrasonic energy in a shorter period of time.

9) The transmit line density of the ultrasound signals. By increasing the transmit line density, the amount of acoustical energy for a given period of time is increased.

10) The imaging mode. When shifting from the triggered imaging mode, it may be preferable to suspend or reset the series progression of frames being imaged. Conversely, the high powered pulses of the triggered imaging mode can be used to burst bubbles. This present the software designer with an elegant solution of simply reversing the mode when the control of the present invention is activated, e.g., when in the triggered imaging mode, entering the low power imaging mode upon activation of the control and vice versa.

FIG. 2a is a signal chart showing the acoustic power during a low power imaging mode as controlled by the waveform control routine 36 in accordance with the preferred embodiment of the present invention. As noted above the simplest, and perhaps most preferred, method of disrupting contrast agent is to simply raise the power of the output waveform. Thus, in its simplest form, the only parameter controlled by the waveform control routine 36 (as implemented for low power imaging modes) is the magnitude of the transmitted pulses. However, those of ordinary skill in the art will, in conjunction with the list set forth above, realize that other parameters can be modified, in and of themselves or, in conjunction with adjusting the power.

During an ultrasound session, a sonographer typically starts with a preliminary scan to locate the ROI and set image controls, such as power level, to provide the best image of the ROI. Next, a contrast agent is injected into the patient and the sonographer watches the agent flow into the ROI. In FIG. 2a, this period is represented as the period between time $t_0$ and $t_1$. Once the sonographer is satisfied with the displayed image, he or she activates the waveform control routine 36 at time $t_1$.

Once activated, the waveform control routine 36 increases the power level of the ultrasound signal output by the transducer array 14 from the level $P_1$ set by the operator to a preset level $P_2$. This increase is typically performed by instructing the pulse generator 16 to output pulses at the preset level $P_2$. The preset level $P_2$ may be stored in memory 38, set using a dedicated control, provided directly by the sonographer pressing or releasing a button, or simply correspond to a maximum power level. As noted above, the waveform control routine can simply activate the triggered imaging mode.

The waveform control routine 36 continues to cause the transducer array 14 to output at the preset level $P_2$ for a defined time period i. The defined time period i may be stored in memory 38, provided by the sonographer, or be calculated based on an analysis of received echos (for example showing that all present contrast agent has been destroyed).

After the defined time period i, at a time $t_2$, the waveform control routine 36 reduces the power level of the signal output by the transducer array 14. In the example shown in FIG. 2 the power level is dropped to $P_1$, the power level originally set by the sonographer. However, those of ordinary skill in the art will recognize that the power level at time $t_2$ may be set from a value in memory 38 or may be calculated based on an analysis of received echos. Once the power level has been reduced, the waveform control routine 36 returns control of the ultrasound system 100 to the control routines 34 for subsequent imaging.

FIG. 2b is a signal chart showing the acoustic power during a low power imaging mode as controlled by the waveform control routine 36 in accordance with another aspect of the preferred embodiment of the present invention. The waveform control routine 36 may be modified to ramp the power level up and/or down over a defined period of time to provide a more gentle, and possibly safer, procedure. Such ramping up and/or down is preferably performed over a series of frames. FIG. 2b shows one possible configuration using three steps to reach the increased power level. The number of steps can be varied based on the ultrasonic system 100, the chosen increased power level and other factors, including clinic trials.

Those of ordinary skill in the art will recognize that the signal charts in FIGS. 2a and 2b are highly idealized. The power levels during the pre-examination period, from $t_0$ to $t_1$, will vary as the sonographer identifies the optimum power level for imaging. Further, the increase in power at time $t_1$ and the decrease in power at time $t_2$ (or the steps thereof in FIG. 2b) do not happen instantaneously. Finally, those skilled in the art will recognize that the time lines in FIGS. 2a and 2b are not to scale or meant to represent actual times used in the present invention, but are rather chosen for clarity of explanation.

Figure 2C:
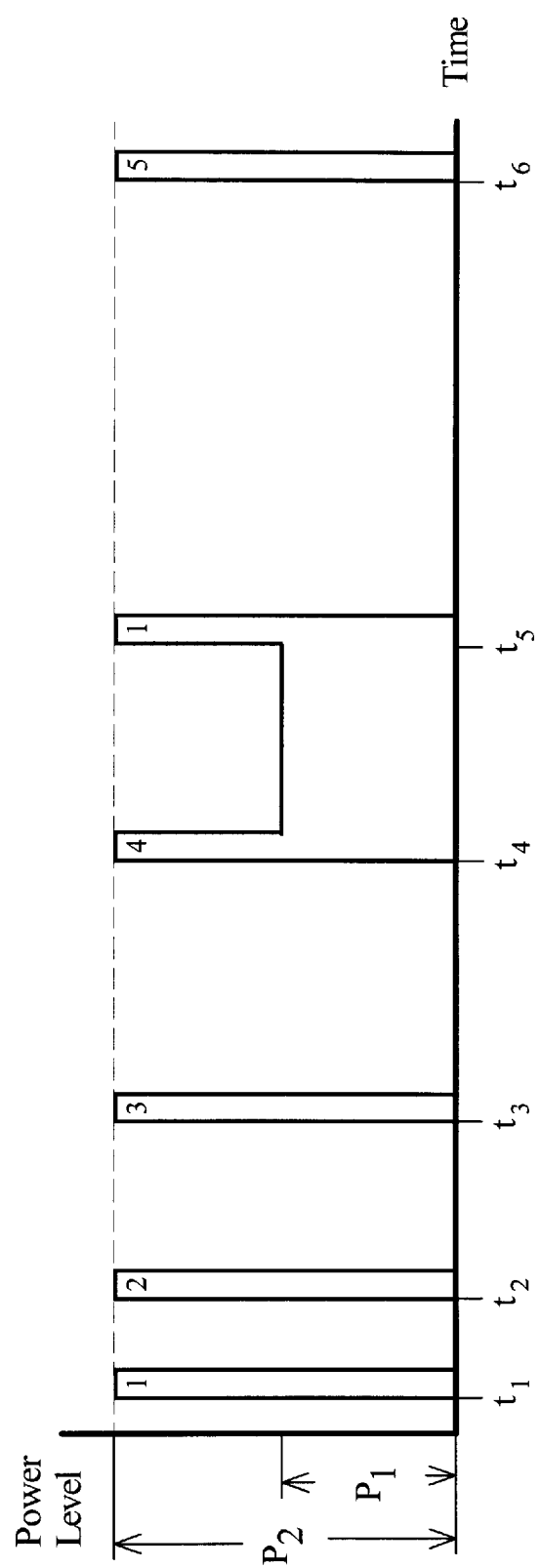
FIG. 2c is a signal chart showing the acoustic power during a triggered imaging mode as controlled by the waveform control routine in accordance with a preferred embodiment of the present invention.

FIG. 2c is a signal chart showing the acoustic power during a triggered imaging mode as controlled by the waveform control routine in accordance with the preferred embodiment of the present invention. In the triggered mode, a sequence is started at time $t_1$ with pulse 1, having a power level $P_2$, being output. One heartbeat later, at time $t_2$, pulse 2 is output. Two heartbeats after pulse 2, at time $t_3$, pulse 3 is output. Subsequently, at time $t_4$ (three heartbeats after pulse 3), pulse 4 is output. At this point, the sonographer determines that he or she needs to check the imaging plane in real time and activates the waveform control routine 36. Thereafter, a waveform having a power level of $P_1$ is output as in a low power imaging mode. At time $t_5$, the system returns to the triggered imaging mode and reissues a first pulse (pulse 1). Picking up where the sequence left off, a pulse 5 is issued four heartbeats later at time $t_6$.

While the foregoing discussion focused on increasing the magnitude of the transmitted pulses, those of ordinary skill in the art will recognize that the other parameters, either singly or in combination, listed above can just as easily be adjusted by the waveform control routine 36 so as to provide an optimal image.

Figure 3:
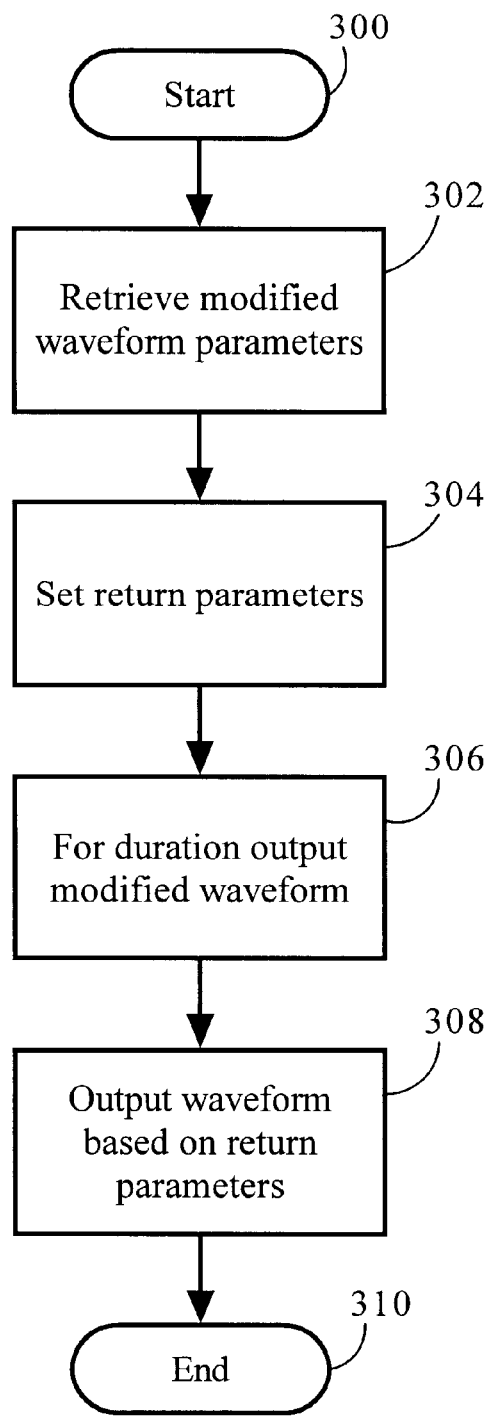
FIG. 3 is a flow chart of a method in accordance with a preferred embodiment of the present invention.

FIG. 3 is a flow chart of a method in accordance with a preferred embodiment of the present invention. The method shown in FIG. 3 is, perhaps, more suited to the low power imaging mode wherein the modified waveform is a destructive waveform for efficiently bursting contrast agent. The method starts at step 300 when the waveform control routine 36 is activated, either by an ultrasound operator or another control routine 34. Then in step 302, the modified waveform parameters, for example a power level, an envelope shape, a transmit cycle, an imaging mode, and /or a line density are retrieved. In this embodiment, one of the parameters includes a duration of the modified waveform. These values can be retrieved from memory 38 (such as system variables updated by the control routines 34) or depending on the configuration of the ultrasound system 100 by monitoring controls set by the sonographer.

Next, in step 304, return waveform parameters are set, this is the waveform to which the output of the transducer array 14 will return after the duration, for example at time $t_2$ in FIG. 2. These may be set to the current values of the affected parameters, retrieved from memory 38, or may be otherwise calculated, for example in the case of adjusting the power, the calculation can take into effect the current power level, the increased power level, the imaging mode and/or characteristics of the ultrasound system. Alternatively, the return parameters can be interactively calculated during the subsequent return (step 308) based on the return echos.

Next, in step 306, the waveform control routine 36 adjusts the parameters controlling the output of the transducer array 14 so as to adopt the desired modified waveform. For example, in the case of the embodiment shown in FIG. 2b, the waveform control routine 36 causes the power level to increase incrementally over a period of time (either stored in memory or set by the operator). After the duration, in step 308, the waveform control routine 36 adjusts the parameters controlling the output of the transducer array 14 so as to adopt the values set in step 304 (or as interactively calculated ). The process ends in step 310 with the return of control to the control routines 34.

Figure 4:
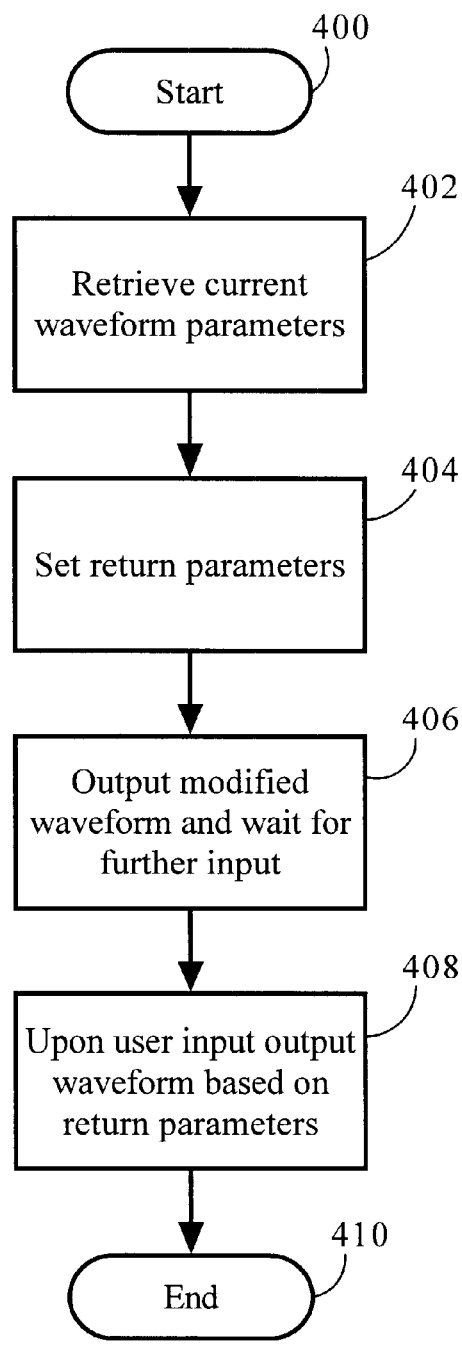
FIG. 4 is a flow chart of a method in accordance with another preferred embodiment of the present invention.

FIG. 4 is a flow chart of a method in accordance with another preferred embodiment of the present invention. In this embodiment the sonographer interactively controls the duration by manually indicating when the disruption waveform should end. The method shown in FIG. 4 is, perhaps, more suited to the triggered imaging mode wherein the modified waveform is a low power waveform for real time viewing. The method starts at step 400 when the waveform control routine 36 is activated by a sonographer, for example, by pressing a button. Then, in step 402, the modified waveform parameters, for example a power level, an envelope shape, a transmit cycle, an imaging mode, and/or a line density are retrieved. In this embodiment, the duration of the modified waveform is not set. The retrieved values can be read from the memory 38 (such as system variables updated by the control routines 34) or depending on the configuration of the ultrasound system 100 by monitoring controls manipulated by the sonographer.

Next, in step 404, return waveform parameters are set, this is the waveform to which the output of the transducer array 14 will return upon completion of the disruption cycle, for example at time $t_5$ in FIG. 2c. These may be set to the current values of the affected parameters, retrieved from the memory 38, or may be otherwise calculated, for example in the case of adjusting the power, the calculation can take into effect the current power level, the increased power level, the imaging mode and/or characteristics of the ultrasound system. Alternatively, the return parameters can be interactively calculated during the subsequent return (step 408) based on the return echos.

Next, in step 406, the waveform control routine 36 adjusts the parameters controlling the output of the transducer array 14 so as to adopt the desired disruption waveform and maintains the waveform until further input is received from the user. In the case of the triggered imaging mode, the system may simply be switched into a low power imaging mode. The process waits for further input, in step 408. For example, such input can comprise the operator pressing or releasing a button used to activate the waveform control routine 36. Upon further input, the waveform control routine 36 adjusts the parameters controlling the output of the transducer array 14 so as to adopt the values set in step 404 (or as interactively calculated). The process ends in step 410 with the return of control to the control routines 34.

Figure 5:
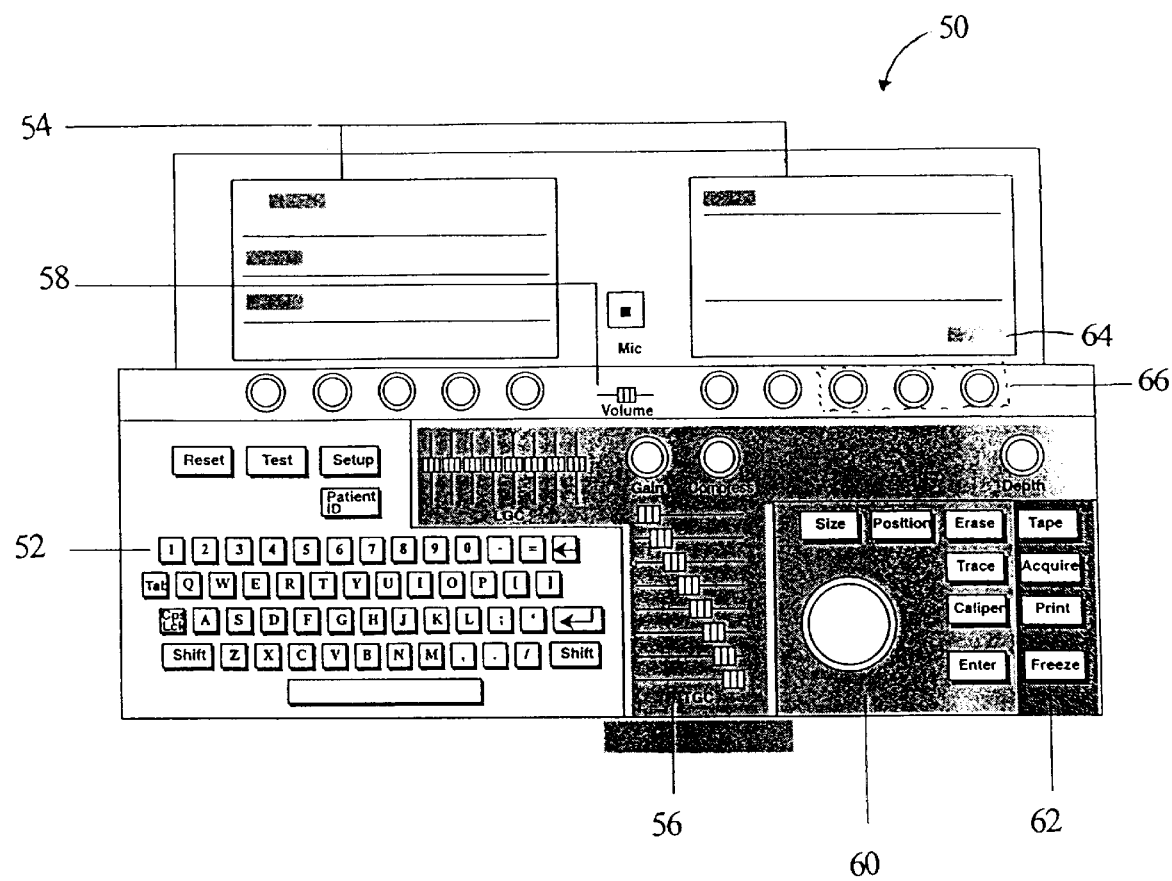
FIG. 5 is a diagram showing an example of the layout of a user control board in an ultrasound system configurable in accordance with the preferred embodiments of the present invention.

FIG. 5 is a diagram showing an example of the layout of a user control board 50 in an ultrasound system configurable in accordance with the preferred embodiment of the present invention. The user control board 50 generally comprises a keyboard 52 and touch screens 54. The keyboard 52 allows general user input based on prompts shown on the touch screens 54. The touch screens 54 not only display information and prompts but, in a known manner, provide an input mechanism, easily configurable by software, such as the control routines 34 and the waveform control routine 36 (see FIG. 1).

A group of specific purpose controls are also provided on the user control board 50. Image tuning controls 56 are provided to allow a sonographer to adjust the ultrasound beam. Such controls, as discussed above, are analog style controls allowing the input of a range of values by sliding or turning the appropriate control. A volume control 58 is provided to allow a sonographer to hear a representation of the ultrasound signal. Measurement and trackball controls 60 are provided to facilitate user selection of a ROI. Hardcopy and loop controls 62 allow the user to select storage options, such as printing or recording to a VCR.

Controls to activate the waveform control routine 36 may be provided in a variety of locations on the user control board 50. A preferred configuration is to associate a soft key 64 on the touch screens 54 with the waveform control routine 36. The soft key can be programmed to activate in either the low power imaging mode or the triggered imaging mode. For example, if the ultrasound system is in the low power imaging mode, the key could select the procedure described in FIG. 3. Conversely, if the ultrasound system is in the triggered imaging mode, the key could select the procedure described in FIG. 4.

As an example, for the disruption of contrast agent during a low power scan, the sonographer would start with a preliminary scan to locate the ROI and set image controls, such as power level, to provide the best image of the ROI. Next, contrast agent is inserted into the patient and the sonographer watches the agent flow into the ROI. Once the sonographer is satisfied with the displayed image, he or she activates the waveform control routine 36 by pressing the soft key 64. The waveform control routine 36 can use pre-stored values for destructive waveform parameters, or values may be inputted by the sonographer, for example by using controls 66. The controls 66 may be rotary dials configured to accept a range of input. It may be preferable, as discussed with reference to FIG. 3, to set the various parameters prior to the activation of the waveform control routine 36. It may also be preferable not to preset the duration, but to allow the sonographer to decide the duration during the examination and indicate when to stop outputting the destructive waveform, for example pressing the soft key 64 again, or holding the soft key 64 for so long as the destructive waveform is desired and then releasing the soft key 64 to indicate a return to a waveform suitable for low power viewing. In yet another alternative, the waveform control routine 36 may be activated by a dedicated key on, for example, the keyboard 52.

Figure 6:
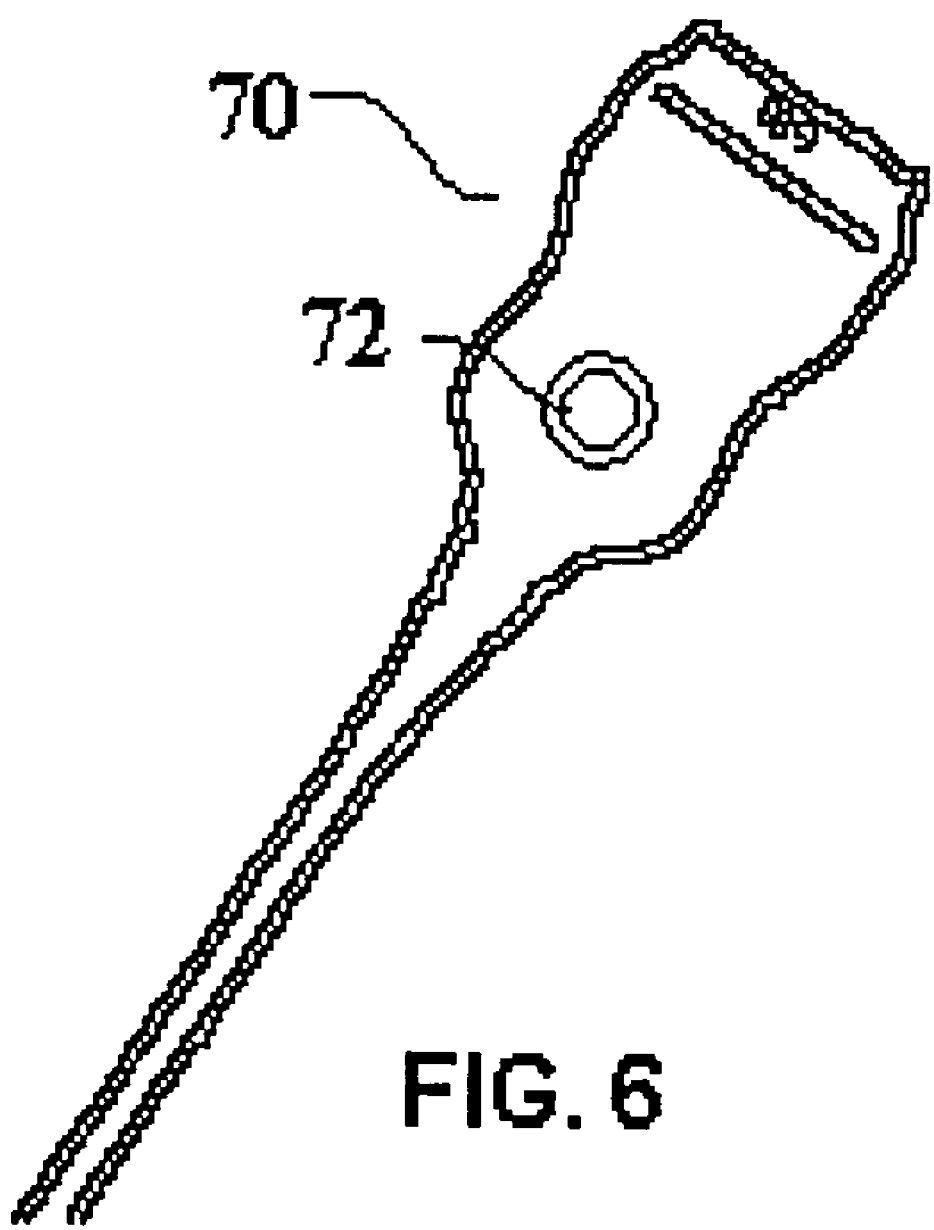
FIG. 6 is a diagram of a transducer configured in accordance with another preferred embodiment of the present invention.

FIG. 6 is a diagram of a transducer 70 configured in accordance with another preferred embodiment of the present invention. A button 72 is provided on the transducer 70 to activate the waveform control routine 36. This may provide some ergonomic benefit in that the sonographer does not have to search the user control board 50 (see FIG. 5) for the specific control to activate the waveform control routine 36. As noted the button 72 may operate in a variety of modes. For example, the button 72 may be configured to call the waveform control routine 36 when pressed. In this case, the waveform control routine 36 automatically determines the duration. Alternatively, the button 72 may be configured to call the waveform control routine 36 when first pressed and to signal the end of the duration when pressed a second time. Similarly, the button 72 may be configured to call the waveform control routine 36 when first pressed and to signal the end of the duration when released.

In accordance with the foregoing, the present inventors have described a user controlled waveform control routine for ultrasound systems. This represents a significant advance over the prior art which required manual control over the power level on the part of Sonographers.

Although a few preferred embodiments of the present invention have been shown and described, it would be appreciated by those skilled in the art that changes may be made in these embodiments without departing from the principles and spirit of the invention, the scope of which is defined in the claims and their equivalents.

What is claimed is:

1. An ultrasound system comprising:
   a transducer that transmits ultrasound signals based on a plurality of parameters defining a first imaging mode;
   a control device that, upon activation during said first imaging mode, adjusts one of a magnitude and fundamental frequency of the transmitted ultrasound pulses, and in addition, at least one additional parameter of the plurality of parameters to cause the transducer to output a modified waveform defining a second imaging mode, and subsequently readjusts the one of magnitude and fundamental frequency of the transmitted ultrasound pulses, and the at least one additional parameter of the plurality of parameters so as to cause the transducer to output a waveform adapted to the first imaging mode.

2. An ultrasound system, as set forth in claim 1, wherein the control device adjusts parameters that control at least one of the following: an envelope shape of a transmitted ultrasound signal pulse train; a frame rate of transmitted ultrasound pulses; a duration of the transmitted ultrasound pulses; a position of a transmit focus; a size and/or sequence of a transmit package; a pulse repetition frequency of transmitted ultrasound pulses; an imaging mode; and a transmit line density.

3. An ultrasound system, as set forth in claim 1, wherein the control device adjusts the at least one additional parameter of the plurality of parameters in sync with at least one of an ECG signal and a start of a sweep by the transducer.

4. An ultrasound system, as set forth in claim 1, wherein the readjustment of the at least one additional parameter of the plurality of parameters occurs after a predetermined time sufficient to scan a predetermined number of frames.

5. An ultrasound system, as set forth in claim 1, wherein the control device is activated by one of: a user touching a screen and pressing a button, and the readjustment of the parameters occurs after one of: a subsequent cessation of said touch, release of said button press, second touch of the screen and second pressing of the button.

6. An ultrasound system, as set forth in claim 1, wherein the control device is activated by a user implementing one of: touching a touch screen and pressing a button.

7. An ultrasound system, as set forth in claim 1, wherein the control device is activated by a diagnostic routine.

8. An ultrasound system, as set forth in claim 1, wherein the control device adjusts parameters to cause an acoustic power level of the transducer to gradually change over several acoustic lines.

9. An ultrasound system comprising:
   a transducer that transmits ultrasound signals based on a plurality of parameters;
   a disruptive waveform routine that, upon activation during a low power imaging mode, adjusts one of a magnitude and fundamental frequency of the transmitted ultrasound signals, and in addition, at least one additional parameter of the plurality of parameters to cause the transducer to output a high power imaging mode waveform that disrupts contrast agent in a region of interest, and subsequently readjusts the one of magnitude and fundamental frequency of the transmitted ultrasound signals and the at least one additional parameter of the plurality of parameters to cause the transducer to output a waveform that allows a user to view the re-introduction of contrast agent to the region of interest; and
   a control interface which receives users inputted commands and data, the control interface providing an activation control that activates the high power imaging mode.

10. An ultrasound system as set forth in claim 9, wherein the disruptive waveform routine is responsive to the activation control and upon one of: release and re-activation thereof readjusts the system to transmit in the low power imaging mode.

11. An ultrasound system, as set forth in claim 9, wherein the activation control is one of: a physical button on the ultrasound system and a touch screen button on a touch screen monitor.

12. An ultrasound system, as set forth in claim 9, wherein the disruptive waveform routine adjusts parameters that control at least one of the following: an envelope shape of a transmitted ultrasound signal pulse train; a frame rate of transmitted ultrasound pulses; a duration of the transmitted ultrasound pulses; a position of a transmit focus; a size and/or sequence of a transmit package; a pulse repetition frequency of transmitted ultrasound pulses; an imaging mode; and a transmit line density.

13. An ultrasound system, as set forth in claim 9, wherein the disruptive waveform routine adjusts the at least one of the plurality of parameters to cause an acoustic power level of the transducer to gradually change over several acoustic lines.

14. An ultrasound system, as set forth in claim 9, wherein the disruptive waveform routine readjusts the one of magnitude and fundamental frequency of the transmitted ultrasound signals, including in addition at least one of the plurality of parameters after a predetermined time.

15. An ultrasound system, as set forth in claim 14, wherein the control interface provides a duration control allowing a user in input a time to be used for the predetermined time.

16. An ultrasound system, as set forth in claim 14, wherein the control interface provides a parameter adjustment control allowing a user to set values for parameters used by the disruptive waveform routine.

17. A method for ultrasound scanning comprising:
   injecting a region of interest with a contrast agent;
   receiving an input from a user to initiate a disruptive waveform; and
   subsequent to receiving the input from the user, without further input from the user, adjusting one of a voltage level and fundamental frequency of a transmission of an ultrasound signal as well as at least one other of a plurality of parameters of the ultrasound signal to produce a disruptive waveform to disrupt contrast agent in a region of interest, and after a predetermined duration, readjusting the one of the voltage level and fundamental frequency, and the at least one other of a plurality of parameters of said signal to allow a user to view the re-introduction of contrast agent to the region of interest.

18. A method for ultrasound scanning comprising:
   injecting a region of interest with a contrast agent;
   receiving an input from a user to initiate a disruptive waveform; and
   subsequent to receiving the input from the user, without further input from the user, adjusting one of a voltage level and fundamental frequency of a transmission of an ultrasound signal as well as at least one other of a plurality of parameters of the ultrasound signal to produce the disruptive waveform to disrupt the contrast agent in a region of interest; and
   when a second input is received from the user, without further input from the user, readjusting the one of the voltage level and the fundamental frequency, and the at least one other of the plurality of parameters to allow a user to view the re-introduction of contrast agent to the region of interest.

19. A method of disrupting contrast agents, comprising:
   directing ultrasonic pulses within a region of interest at a transmit focus within which a contrast agent is present at a first fundamental frequency and first power level; and
   moving the transmit focus, on a line by line basis, within the region of interest to disrupt the contrast agent, where the ultrasonic pulses are transmitted at one of a second fundamental frequency and second power level which are distinct from the first fundamental frequency and first power level, respectively.

20. A method for ultrasound scanning comprising:
   injecting a region of interest with a contrast agent;
   starting a triggered imaging mode sequence;
   receiving an input from a user to initiate a low power imaging mode; and
   subsequent to receiving the input from the user, without further input from the user, adjusting one of a power level and fundamental frequency, and at least one other of a plurality of parameters of an ultrasound signal to produce a low power waveform adapted for low power imaging; and
   when a second input is received from the user, without further input from the user, readjusting the one of the power level and fundamental frequency, and at least one other of the plurality of parameters to continue the triggered imaging mode sequence.

* * * * *